United States Patent

Habeck et al.

[11] Patent Number: 6,159,455
[45] Date of Patent: Dec. 12, 2000

[54] DIMERIC α-ALKYLSTYRENE DERIVATIVES AS PHOTOSTABLE UV FILTERS IN COSMETIC AND PHARMACEUTICAL PREPARATIONS

[75] Inventors: Thorsten Habeck, Meckenheim; Frank Prechtl, Frankfurt; Thomas Wünsch, Speyer; Horst Westenfelder, Neustadt, all of Germany

[73] Assignee: BASF Aktiengesellschaft, Ludwigshafen, Germany

[21] Appl. No.: 09/451,859

[22] Filed: Dec. 1, 1999

[30] Foreign Application Priority Data

Dec. 3, 1998 [DE] Germany .............. 198 55 649

[51] Int. Cl.$^7$ .............. A61K 7/42; A61K 7/44; A61K 7/00
[52] U.S. Cl. .............. 424/59; 424/60; 424/400; 424/401
[58] Field of Search .............. 424/59, 60, 400, 424/401

[56] References Cited

U.S. PATENT DOCUMENTS

| | | | |
|---|---|---|---|
| 3,706,700 | 12/1972 | Kirchmayr et al. | 106/178 |
| 3,824,273 | 7/1974 | Kirchmayr et al. | |
| 4,387,089 | 6/1983 | Depolo | 424/59 |
| 4,749,774 | 6/1988 | Weaver et al. | 528/288 |
| 5,576,354 | 11/1996 | Deflandre et al. | 514/685 |
| 5,587,150 | 12/1996 | Deflandre et al. | 424/59 |

FOREIGN PATENT DOCUMENTS

| | | |
|---|---|---|
| 251398 | 1/1988 | European Pat. Off. . |
| 401128 | 12/1990 | European Pat. Off. . |
| 413648 | 2/1991 | European Pat. Off. . |
| 2440933 | 6/1980 | France . |
| 1568693 | 7/1966 | Germany . |
| 1115596 | 5/1968 | United Kingdom . |
| 91/11989 | 8/1991 | WIPO . |

*Primary Examiner*—Shelley A. Dodson
*Attorney, Agent, or Firm*—Keil & Weinkauf

[57] ABSTRACT

The invention relates to the use of substituted, dimeric α-alkylstyrene derivatives of the formula I

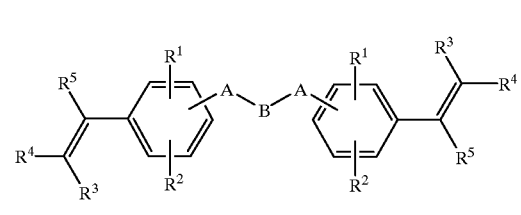

in which the substituents are as defined in the description, as photostable UV filters in cosmetic and pharmaceutical preparations for protecting human skin or human hair against solar rays, alone or together with compounds which absorb in the UV region and which are known per se for cosmetic and pharmaceutical preparations.

6 Claims, No Drawings

DIMERIC α-ALKYLSTYRENE DERIVATIVES AS PHOTOSTABLE UV FILTERS IN COSMETIC AND PHARMACEUTICAL PREPARATIONS

The invention relates to the use of substituted, dimeric α-alkylstyrene derivatives as photostable UV filters in cosmetic or pharmaceutical preparations for protecting the human epidermis or human hair from solar rays, specifically from UV radiation in the range from 320 to 400 nm.

The sunscreens employed in cosmetic and pharmaceutical preparations have the task of preventing, or at least diminishing the consequences of, harmful effects of sunlight on the human skin. However, these sunscreens also serve to protect other ingredients from decomposition or breakdown by UV radiation. In hair cosmetic formulations the aim is to reduce damage to the keratin fibers by UV rays.

The sunlight reaching the surface of the earth contains UV-B radiation (280 to 320 nm) and UV-A radiation (>320 nm), which are directly adjacent to the visible light region. The effect on the human skin is manifested, particularly in the case of UV-B radiation, by sunburn. Accordingly, the industry offers a relatively large number of substances which absorb UV-B radiation and thus prevent sunburn.

Dermatoglogical investigations have now shown that UV-A radiation is also perfectly capable of causing skin damage and allergies by, for example, damaging the keratin or elastin. This reduces the elasticity and water storage capacity of the skin, i.e. the skin becomes less supple and tends to form wrinkles. The noticeably high incidence of skin cancer in regions where insolation is strong shows that damage to the genetic information in the cells is evidently also caused by sunlight, specifically by UV-A radiation. All these findings therefore make it appear necessary to develop efficient filter substances for the UV-A region.

There is a growing demand for sunscreens for cosmetic and pharmaceutical preparations which can be used in particular as UV-A filters and whose absorption maxima ought therefore to be in the range from about 320 to 380 nm. In order to achieve the required effect by using the minimum amount, sunscreens of this type ought additionally to have a high specific extinction. Sunscreens for certain cosmetic products must also meet a large number of other requirements, for example good solubility in cosmetic oils, high stability of the emulsions produced with them, toxicological acceptability, and slight intrinsic odor and slight intrinsic color.

Another requirement which sunscreens must meet is adequate photostability. However, this is only inadequately ensured, if at all, with the UV-A-absorbing sunscreens hitherto available.

French Patent No. 2 440 933 describes 4-(1,1-dimethylethyl)-4'-methoxydibenzoylmethane as a UV-A filter. It is proposed to combine this specific UV-A filter, which is sold by GIVAUDAN under the name "PARSOL 1789", with various UV-B filters in order to absorb all UV rays having a wavelength from 280 to 380 nm.

However, this UV-A filter does not have sufficient photochemical stability, when used alone or in combination with UV-B filters, to ensure sustained protection of the skin during sunbathing for prolonged periods, which means that repeated applications at regular and frequent intervals are required if effective protection of the skin from all UV rays is desired.

For this reason, EP-A-0 514 491 discloses the stabilization of the insufficiently photostable UV-A filters by adding 2-cyano-3,3-diphenylacrylic esters which themselves act as filters in the UV-B region.

It has furthermore already been proposed in EP-A-0 251 398 to combine chromophores absorbing UV-A radiation and UV-B radiation into one molecule by using a linker. This has the disadvantage that, firstly a free combination of UV-A and UV-B filters in the cosmetic preparation is no longer possible, and that difficulties in the chemical linkage of the chromophores allow only certain combinations.

EP-A-0 413 648 describes the use of dimeric, substituted styrene derivatives as UV absorbers in cosmetic suncreens.

EP-A-0 401 128, DE-A-1 568 693 and U.S. Pat. No. 4,749,774 each describe the use of dimeric, substituted styrene derivatives as UV absorbers in plastics, for example in packaging materials for beverages and foods.

The dimeric styrene derivatives disclosed in the above patent specifications do not, however, exhibit sufficient photostability.

It is an object of the invention to propose suncreens for cosmetic and pharmaceutical purposes which absorb in the UV-A region with high absorbance, which are photostable, have low intrinsic coloration, i.e. a sharp band structure and, depending on the substituent, are soluble in oil or water.

We have found that this object is achieved by using substituted, dimeric α-alkylstyrene derivatives of the formula I

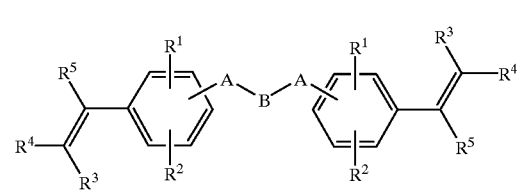

in which the substituents independently of one another have the following meanings:

$R^1$ and $R^2$ are hydrogen, OH, $NH_2$, $C_1$–$C_{12}$-alkyl, $C_1$–$C_{12}$-alkoxy, $C_1$–$C_{12}$-alkylamino, $C_1$–$C_{12}$-dialkylamino, substituents which confer solubility in water, chosen from the group consisting of carboxylate, sulfonate or ammonium radicals;

$R^3$ is $COOR^6$, $COR^6$, $CONR^6R^7$, CN;

$R^4$ is $COOR^6$, $COR^6$, $CONR^6R^7$, CN;

$R^5$ is $C_1$–$C_{12}$-alkyl, $R^6$ and $R^7$ are hydrogen, $C_1$–$C_{12}$-alkyl, $C_2$–$C_{10}$-alkenyl, $C_3$–$C_{10}$-cycloalkyl, $C_3$–$C_{10}$-cycloalkenyl, aryl, heteroaryl, optionally substituted;

A is O, S, N—$R^8$;

B is $C_1$–$C_{12}$-alkylene, $C_4$–$C_{12}$-cycloalkylene, $C_8$–$C_{22}$-aralkylene, $C_9$–$C_{21}$-monooxoaralkylene, [—X—]$_n$—Y—;

$R^8$ is hydrogen, $C_1$–$C_{12}$-alkyl;

X is —$CH_2$—$CH_2$—Z—, —$CH_2$—$CH_2$—$CH_2$—Z—, —$CH(CH_3)$—$CH_2$—Z—, —$CH_2$—$CH_2$—$CH_2$—$CH_2$—Z—, —$CH_2$—$CH(CH_2$—$CH_3)$—Z—;

Y is —$CH_2$—$CH_2$—, —$CH_2$—$CH_2$—$CH_2$—, —$CH(CH_3)$—$CH_2$—, —$CH_2$—$CH_2$—$CH_2$—$CH_2$—, —$CH_2$—$CH(CH_2$—$CH_3)$—;

Z is O, S;

n is 1 to 150, where, in each case, two of the radicals $R^1$, $R^2$ and $R^8$ together with the aromatic ring to which they are bonded can form a 5- or 6-membered ring, as photostable UV filters in cosmetic and pharmaceutical preparations for protecting human skin or human hair from solar rays, alone or together with compounds which absorb in the UV region and which are known per se for cosmetic and pharmaceutical preparations.

Alkyl radicals $R^1$ and $R^2$ and also $R^6$ to $R^8$ which may be mentioned are branched or unbranched $C_1$–$C_{12}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl and n-dodecyl.

Alkenyl radicals $R^6$ and $R^7$ which may be mentioned are branched $C_2$–$C_{10}$-alkenyl chains, preferably ethenyl, n-propenyl, 1-methylethenyl, n-butenyl, 1-methylpropenyl, 2-methylpropenyl, 1,1-dimethylethenyl, n-pentenyl, 1-methylbutenyl, 2-methylbutenyl, 3-methylbutenyl, 2,2-dimethylpropenyl, 1-ethylpropenyl, n-hexenyl, 1,1-dimethylpropenyl, 1,2-dimethylpropenyl, 1-methylpentenyl, 2-methylpentenyl, 3-methylpentenyl, 4-methylpentenyl, 1,1-dimethylbutenyl, 1,2-dimethylbutenyl, 1,3-dimethylbutenenyl, 2,2-dimethylbutenyl, 2,3-dimethylbutenyl, 3,3-dimethylbutenyl, 1-ethylbutenyl, 2-ethylbutenyl, 1,1,2-trimethylpropenyl, 1,2,2-trimethylpropenyl, 1-ethyl-1-methylpropenyl, 1-ethyl-2-methylpropenyl, n-heptenyl, n-octenyl, n-nonenyl, n-decenyl.

Cycloalkyl radicals $R^6$ and $R^7$ which may be mentioned are branched or unbranched $C_3$–$C_{10}$-cycloalkyl chains, preferably cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclypropyl, 1-methyl-2-ethylcyclopropyl, cyclooctyl, cyclononyl or cyclodecyl.

Cycloalkenyl radicals $R^6$ and $R^7$ which may be mentioned are branched or unbranched $C_3$–$C_{10}$-cycloalkenyl chains having one or more double bonds such as cyclopropenyl, cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctatetraenyl, cyclononenyl or cyclodecyl.

The cycloalkenyl and cycloalkyl radicals can optionally be substituted by one or more, e.g. from 1 to 3, radicals such as halogen, e.g. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals, or may contain in the ring from 1 to 3 hetero atoms such as sulfur, nitrogen, whose free valences may be saturated by hydrogen or $C_1$–$C_4$-alkyl, or oxygen.

Suitable alkoxy radicals $R^1$ and $R^2$ are those having from 1 to 12 carbon atoms, preferably with from 4 to 8 carbon atoms.

Examples which may be mentioned are:

| | |
|---|---|
| methoxy | ethoxy |
| n-propoxy | isopropoxy |
| 1-methylpropoxy | n-butoxy |
| n-pentoxy | 2-methylpropoxy |
| 3-methylbutoxy | 1,1-dimethylpropoxy |
| 2,2-dimethylpropoxy | hexoxy |
| 1-methyl-1-ethylpropoxy | heptoxy |
| octoxy | 2-ethylhexoxy |

Suitable mono- or dialkylamino radicals $R^1$ and $R^2$ are those which contain alkyl radicals having from 1 to 12 carbon atoms, preferably from 1 to 8 carbon atoms, for example methyl, n-propyl, n-butyl, 2-methylpropyl, 1,1-dimethylpropyl, hexyl, heptyl, 2-ethylhexyl, isopropyl, 1-methylpropyl, n-pentyl, 3-methylbutyl, 2,2-dimethylpropyl, 1-methyl-1-ethylpropyl and octyl.

Aryl for $R^6$ and $R^7$ is taken to mean aromatic rings or ring systems having from 6 to 18 carbon atoms in the ring system, for example phenyl or naphthyl, each of which can optionally be substituted by one or more radicals such as halogen, e.g. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals. Preference is given to optionally substituted phenyl, methoxyphenyl and naphthyl.

Heteroaryl radicals for $R^6$ and $R^7$ are advantageously single or fused aromatic ring systems having one or more heteroaromatic 3- to 7-membered rings. Hetero atoms which may be present in the ring or ring system are one or more nitrogen, sulfur and/or oxygen atoms.

Hydrophilic radicals $R^1$ and $R^2$, i.e. radicals which enable the compounds of the formula I to dissolve in water, are, for example, carboxyl and sulfoxy radicals and in particular salts thereof with any physiologically tolerable cations, such as the alkali metal salts or such as the trialkylammonium salts, such as tri(hydroxyalkyl)ammonium salts or the 2-methylpropan-1-ol-2-ammonium salts. Also suitable are ammonium radicals, in particular alkylammonium radicals with any physiologically tolerable anions.

Alkylene radicals B which may be mentioned are branched or unbranched $C_1$–$C_{12}$-alkylene chains, preferably methylene, ethylene, n-propylene, 1-methylethylene, n-butylene, 1-methylpropylene, 2-methylpropylene, 1,1-dimethylethylene, n-pentylene, 1-methylbutylene, 2-methylbutylene, 3-methylbutylene, 2,2-dimethylpropylene, 1-ethylpropylene, n-hexylene, 1,1-dimethylpropylene, 1,2-dimethylpropylene, 1-methylpentylene, 2-methylpentylene, 3-methylpentylene, 4-methylpentylene, 1,1-dimethylbutylene, 1,2-dimethylbutylene, 1,3-dimethylbutylene, 2,2-dimethylbutylene, 2,3-dimethylbutylene, 3,3-dimethylbutylene, 1-ethylbutylene, 2-ethylbutylene, 1,1,2-trimethylpropylene, 1,2,2-trimethylpropylene, 1-ethyl-1-methylpropylene, 1-ethyl-2-methylpropylene, n-heptylene, n-octylene, n-nonylene, n-decylene, n-undecylene and n-dodecylene.

The abovementioned alkylene radicals can optionally be mono- or polysubstituted. Possible substituents are the following groups: OH, O—$C_1$–$C_6$-acyl, O—$C_1$–$C_6$-alkyl, $NH_2$, NH—$C_1$–$C_6$-alkyl, NH—$C_1$–$C_6$-acyl, CN, COOH, COO—$C_1$–$C_6$-alkyl.

Als Cycloalkylene radicals B which may be mentioned are $C_4$–$C_{12}$-cycloalkylene radical or example

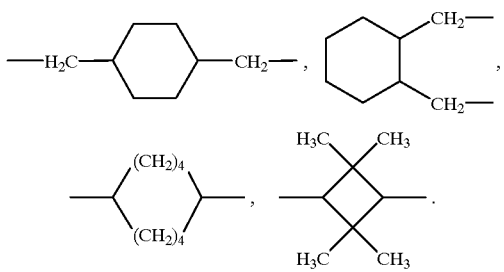

Aralkylene radicals B which may be mentioned are $C_8$–$C_{22}$-aralkylene radicals, for example

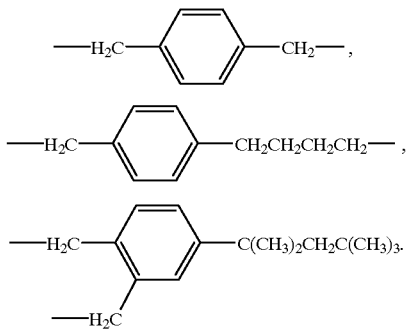

Monooxoaralkylene radicals B which may be mentioned are $C_9$–$C_{21}$-monooxoaralkylene radicals, for example

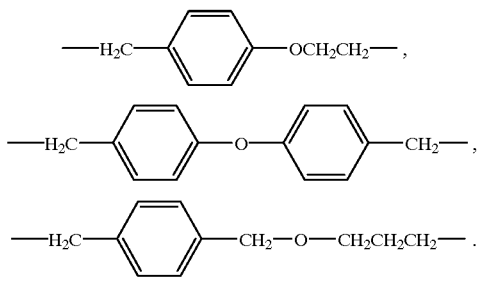

The radical $[-X-]_n-Y-$ is dimeric or polymeric $C_2$–$C_4$-alkyl ethers, $C_2$–$C_4$-alkyl thioethers or $C_2$–$C_4$-alkylimines having from 2 to 151 alternating monomer units. Preference is given to dimeric or polymeric $C_2$–$C_4$-alkyl ethers having from 2 to 21 alternating monomer units, and very particular preference is given to dimeric or polymeric ethylene glycols or propylene glycols having from 2 to 21 alternating monomer units.

In each case two of the radicals $R^1$, $R^2$ and $R^8$ can, together with the aromatic ring to which they are bonded, form a further 5- or 6-membered ring. Examples thereof are the following structures:

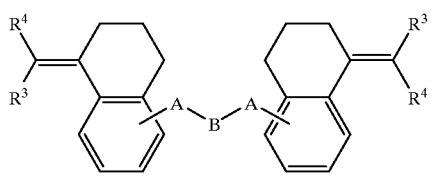

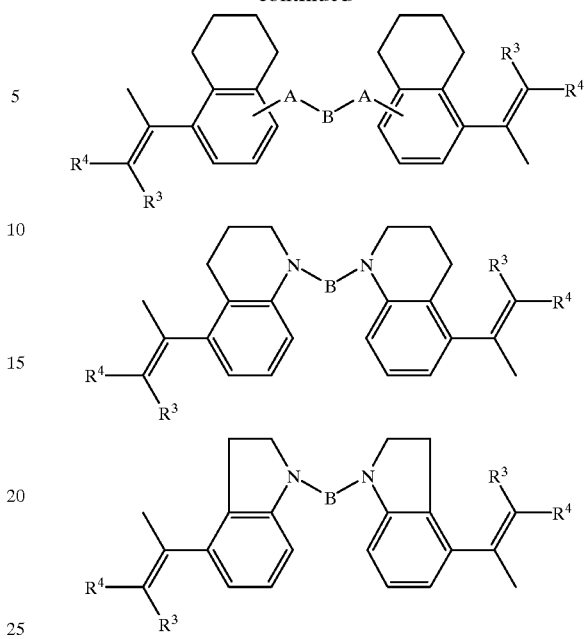

Preference is given to compounds of the formula I in which $R^1$ and $R^2$ are hydrogen, $C_1$–$C_8$-alkyl, $C_1$–$C_8$-alkoxy, substituents which confer solubility in water, chosen from the group consisting of carboxylate, sulfonate or ammonium radicals;

$R^3$ is $COOR^6$, CN;

$R^4$ is $COOR^6$, CN;

$R^5$ is $C_1$–$C_6$-alkyl;

$R^6$ is $C_1$–$C_{12}$-alkyl;

A is O;

B is $C_1$–$C_{12}$-alkylene, $C_8$–$C_{22}$-aralkylene, $C_4$–$C_{12}$-cycloalkylene, $[-X-]_n-Y$;

X is $-CH_2-CH_2-O-$, $-CH_2-CH_2-CH_2-O-$, $-CH(CH_3)-CH_2-O-$, $-CH_2-CH_2-CH_2-CH_2-O-$, $-CH_2-CH(CH_2-CH_3)-O-$;

Y is $-CH_2-CH_2-$, $-CH_2-CH_2-CH_2-$, $-CH(CH_3)-CH_2-$, $-CH_2-CH_2-CH_2-CH_2-$, $-CH_2-CH(CH_2-CH_3)-$;

n is 1 to 20.

Particular preference is given to those compounds of the formula I in which $R^1$ and $R^2$ are hydrogen, $C_4$–$C_8$-alkyl, $C_4$–$C_8$-alkoxy, substituents which confer solubility in water, chosen from the group consisting of carboxylate, sulfonate or ammonium radicals;

$R^3$ and $R^4$ CN;

$R^5$ is $C_1$–$C_6$-alkyl;

A is O;

B is $C_1$–$C_{12}$-alkylene, $[-X-]_n-Y$;

X is $-CH_2-CH_2-O-$, $-CH(CH_3)-CH_2-O-$;

Y is $-CH_2-CH_2-$, $-CH(CH_3)-CH_2-$;

n is 1 to 20.

The group —A—B—A—can in each case bonded in the ortho, meta or para position on the aromatic compound, relative to the radical containing $R^3$ to $R^5$. Particular preference is given to compounds of the formula I in which —A—B—A—is in the para-position. Very particular preference is given to those substituted, dimeric α-alkylstyrene derivatives of the following structural formula Ia

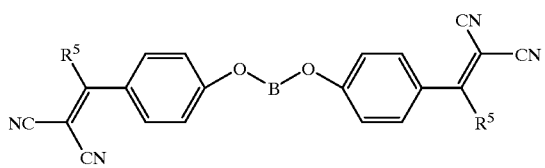

Ia where the substituents have the following meaning:

$R^5$ is $C_1$–$C_6$-alkyl, preferably methyl;

B is $C_1$–$C_{12}$-alkylene.

For example, the compounds of the formula I listed below in Table 1 have particular photostable properties.

TABLE 1

I

| B |
|---|
| —[CH$_2$]$_2$— |
| —[CH$_2$]$_3$— |
| —[CH$_2$]$_4$— |
| —[CH$_2$]$_5$— |
| —[CH$_2$]$_6$— |
| —CH$_2$—CH$_2$—CH(CH$_3$)—CH$_2$—CH$_2$— |
| —CH$_2$—C(CH$_3$)$_2$—CH$_2$— |
| —CH$_2$—CH(OH)—CH$_2$— |
| —CH$_2$—CH(OH)CH(OH)—CH$_2$— |
| —[CH$_2$]$_7$— |
| —[CH$_2$]$_8$— |
| —[CH$_2$]$_9$— |
| —[CH$_2$]$_{10}$— |
| —H$_2$C–⟨cyclohexyl⟩–CH$_2$— |
| —CH$_2$–⟨cyclohexyl⟩–CH$_2$— |

The compounds of the formula I to be used according to the invention can, for example, be prepared according to the following reaction equation

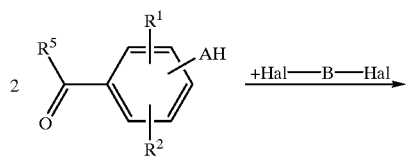

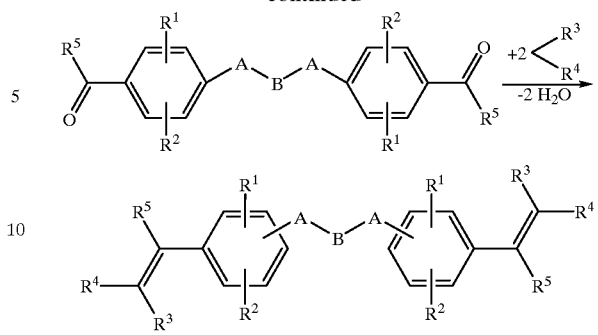

where Hal is halogen, for example chlorine or bromine, and $R^1$ to $R^5$ and the variables A and B are as defined in claim 1.

The present invention further provides cosmetic and pharmaceutical preparations which comprise from 0.1 to 10% by weight, preferably from 1 to 7% by weight, based on the total amount of the cosmetic and pharmaceutical preparation, of one or more of the compounds of the formula I together with compounds which absorb in the UV-B region and which are known per se for cosmetic and pharmaceutical preparations as a sunscreen, the compounds of the formula I generally being used in a smaller amount than the UV-B-absorbing compounds.

Preference is given to the above cosmetic and pharmaceutical preparations which comprise one or more of the compounds of the formula Ia

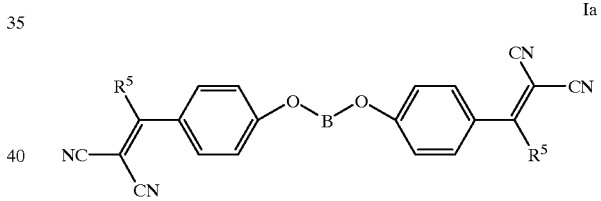

Ia where the substituents have the following meanings:

$R^5$ is $C_1$–$C_6$-alkyl, preferably methyl; and

B is $C_1$–$C_{12}$-alkylene.

Most of the sunscreens in the cosmetic and pharmaceutical preparations used to protect the human epidermis consist of compounds which absorb UV light in the UV-B region, i.e. in the range from 280 to 320 nm. For example, the amount of UV-A absorbers to be used according to the invention is from 10 to 90% by weight, preferably from 20 to 50% by weight, based on the total amount of UV-B- and UV-A-absorbing substances.

The cosmetic and pharmaceutical preparations comprising sunscreens are normally based on a carrier which comprises at least one oil phase. However, preparations based on water alone are also suitable if compounds with hydrophilic substituents are used. Accordingly, suitable preparations are oils, oil-in-water and water-in-oil emulsions, creams and pastes, lip-protection stick compositions or fat-free gels.

Such sunscreen preparations can accordingly be in liquid, paste or solid form, for example as water-in-oil creams, oil-in-water creams and lotions, aerosol foam creams, gels, oils, grease sticks, powders, sprays or alcoholic/aqueous lotions.

Examples of conventional oil components in cosmetics are liquid paraffin, glyceryl stearate, isopropyl myristate, diisopropyl adipate, cetylstearyl 2-ethylhexanoate, hydrogenated polyisobutene, vaseline, caprylic acid/capric acid triglycerides, microcrystalline wax, lanolin and stearic acid.

Examples of conventional cosmetic auxiliaries which may be suitable as additives are coemulsifiers, fats and waxes, stabilizers, thickeners, biogenic active ingredients, film formers, fragrances, dyes, lusterizing agents, preservatives, pigments, electrolytes (e.g. magnesium sulfate) and pH regulators. Suitable coemulsifiers are, preferably, known W/O and also O/W emulsifiers, such as polyglycerol esters, sorbitan esters or partially esterified glycerides. Typical examples of fats are glycerides; waxes which may be mentioned include beeswax, paraffin wax or microwaxes, optionally in combination with hydrophilic waxes. Stabilizers which may be used are metal salts of fatty acids, for example magnesium stearate, aluminum stearate and/or zinc stearate. Examples of suitable thickeners are crosslinked polyacrylic acids and derivatives thereof, polysaccharides, in particular xanthan gum, guar guar, agar agar, alginates and tyloses, carboxymethylcellulose and hydroxyethylcellulose, also fatty alcohols, monoglycerides and fatty acids, polyacrylates, polyvinyl alcohol and polyvinylpyrrolidone. Biogenic active ingredients are taken to mean, for example, plant extracts, protein hydrolysates and vitamin complexes. Examples of traditional film formers are hydrocolloids such as chitosan, microcrystalline chitosan or quaternized chitosan, polyvinylpyrrolidone, vinylpyrrolidone-vinyl acetate copolymers, polymers of the acrylic acid series, quaternary cellulose derivatives and similar compounds. Suitable preservatives are, for example, formaldehyde solution, p-hydroxybenzoate or sorbic acid. Suitable lusterizing agents are, for example, glycol distearic esters, such as ethylene glycol distearate, but also fatty acids and fatty acid monoglycol esters. The colorants which may be used are those substances suitable and approved for cosmetic purposes, such as, for example, those listed in the publication "Kosmetische Farbemittel" from the Farbstoffkommission der Deutschen Forschungsgemeinschaft, published by Verlag Chemie, Weinheim, 1984. These colorants are normally used in concentrations of from 0.001 to 1% by weight, based on the total mixture.

The total amount of auxiliaries and additives can be from 1 to 80% by weight, preferably from 6 to 40% by weight, and the nonaqueous content ("active substance") can be from 20 to 80% by weight, preferably from 30 to 70% by weight, based on the formulation. The formulations can be prepared in a manner known per se, i.e. for example by hot, cold, hot/cold or PIT emulsification. This is purely a mechanical process and there is no chemical reaction.

Finally, it is possible additionally to use further substances known per se which absorb in the UV region, provided they are stable in the overall system of the combination of UV filters to be used according to the invention.

UV filter substances which are used in combination with the compounds of the formula I to be used according to the invention are any UV-A and UV-B filter substances. Examples which may be mentioned are (see Table 2):

TABLE 2

| No. | Substance | CAS No. (=acid) |
|---|---|---|
| 1 | 4-Aminobenzoic acid | 150-13-0 |
| 2 | 3-(4'Trimethylammonio)benzylidene-2-bornanone methylsulfate | 52793-97-2 |
| 3 | 3,3,5-Trimethylcyclohexyl salicylate (homosalate) | 118-56-9 |
| 4 | 2-Hydroxy-4-methoxybenzophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)bis-(7,7-dimethyl-2-oxobicyclo[2.2.1]-heptane-1-methanesulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | Isoamyl 4-methoxycinnamate | 71617-10-2 |
| 11 | 2-Ethylhexyl 4-methoxycinnamate | 5466-77-3 |
| 12 | 2-Hydroxy-4-methoxybenzophenone-5-sulfonic acid (sulisobenzone) and the sodium salt | 4065-45-6 |
| 13 | 3-(4'-Methylbenzylidene)-2-bornanone | 36861-47-9 |
| 14 | 3-Benzylidene-2-bornanone | 15087-24-8 |
| 15 | 1-(4'-Isopropylphenyl)-3-phenyl-1,3-propanedione | 63250-25-9 |
| 16 | 4-Isopropylbenzyl salicylate | 94134-93-7 |
| 17 | 3-(4-Imidazolyl)acrylic acid and its ethyl ester | 104-98-3 |
| 18 | Ethyl 2-cyano-3,3-diphenylacrylate | 5232-99-5 |
| 19 | 2'-Ethylhexyl 2-cyano-3,3-diphenylacrylate | 6197-30-4 |
| 20 | Menthyl o-aminobenzoate or 5-menthyl 2-aminobenzoate | 134-09-8 |
| 21 | Glyceryl p-aminobenzoate or 1-glyceryl 4-aminobenzoate | 136-44-7 |
| 22 | 2,2'-Dihydroxy-4-methoxybenzophenone (dioxybenzone) | 131-53-3 |
| 23 | 2-Hydroxy-4-methoxy-4-methylbenzophenone (mexonone) | 1641-17-4 |
| 24 | Triethanolamine salicylate | 2174-16-5 |
| 25 | Dimethoxyphenylglyoxalic acid or sodium 3,4-dimethoxyphenylglyoxalate | 4732-70-1 |
| 26 | 3-(4'Sulfobenzylidene)-2-bornanone and its salts | 56039-58-8 |
| 27 | 4-tert-Butyl-4'-methoxydibenzoylmethane | 70356-09-1 |
| 28 | 2,2',4,4'-Tetrahydroxybenzophenone | 131-55-5 |
| 29 | Bis,bis(2-ethylhexyl) 4,4'-[[6-[[4-[[(1,1-dimethylethyl)amino]carbonyl]-phenyl]amino]-1,3,5-triazine-2,4-diyl]diimino]-benzoate | 154702-15-5 |
| 30 | 2-(2H-Benzotriazol-2-yl)-4-methyl-6-[2-methyl-3-[1,3,3,3-tetramethyl-1-[(trimethylsilyl)-oxy]disiloxanyl]propyl]phenol | 155633-54-8 |
| 31 | Dimethicone diethylbenzalmalonate | 207574-74-1 |
| 32 | Bis[2-hydroxy-5-tert-octyl-3-(benzotriazol-2-yl)phenyl]methane (Bisoctyltriazone) | 103597-45-1 |
| 33 | 1H-Benzimidazole-4,6-disulfonic acid, 2,2'-(1,4-phenylene)bis-, Disodium salt (Benzimidazylate) | 180898-37-7 |
| 34 | Phenol, 2,2'-[6-(4-methoxyphenyl)-1,3,5-triazine-2,4-diyl]bis[5-[(2-ethylhexyl)oxy] (Aniso Triazine) | 187393-00-6 |

Finally, micronized pigments such as titanium dioxide and zinc oxide can also be mentioned.

To protect human hair against UV rays, the sunscreens of the formula I according to the invention can be incorporated into shampoos, lotions, gels, hairsprays, aerosol foam creams or emulsions in concentrations of from 0.1 to 10% by weight, preferably from 1 to 7% by weight. The formulations in each case can be used inter alia for washing, coloring and for styling the hair.

The compounds to be used according to the invention are usually notable for a particularly high absorptive power in the UV-A radiation range with sharp band structure. Furthermore, they are readily soluble in cosmetic oils and can be incorporated easily into cosmetic formulations. The emulsions prepared using the compounds I are particularly notable for high stability, the compounds I themselves for high photostability, and the preparations prepared using I for their pleasant feel on the skin.

The UV filter action of the novel compounds of the formula I can also be utilized for stabilizing active ingredients and auxiliaries in cosmetic and pharmaceutical formulations.

EXAMPLES

I. PREPARATION

Example 1

Preparation Procedure for Compound No. 2 in Table 2 a) 0.5 mol of 4-hydroxyacetophenone, 0.25 mol of 1,4-dibrombutane and 0.5 mol of potassium carbonate were heated at 80° C. in 200 ml of dimethylformamide for 4 h. 600 ml of water were added to the mixture, which was stirred at room temperature for 30 min, the product precipitating out. The precipitate was filtered off with suction, washed with 3×100 ml of water and dried under reduced pressure (200 mbar) at 50° C. Yield: 68 g (83% of theory) of the dimeric acetophenone of the following formula:

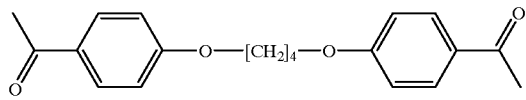

b) 65.2 g (0.2 mol) of the compound from Example 1a and 26.4 g (0.4 mol) of malononitrile were dissolved in 500 ml of toluene, and 9.2 g of each of phenoxyacetic acid and salicylic acid were added. The mixture was heated to 60° C. and ammonia was introduced until saturation. The reaction mixture was then refluxed for 3 h, the water of reaction which formed being removed. The precipitate which formed was filtered off with suction, and then thoroughly washed with 100 ml of each of methanol and water. The product was then dried under reduced pressure (200 mbar) at 50° C. Yield: 73 g (86% of theory).

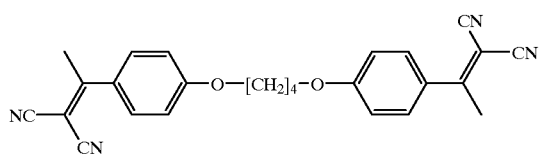

Compounds 1 and 3 to 6 in Table 3 are prepared as in Example 1.

TABLE 3

Dimeric hydroxyacetophenone condensates

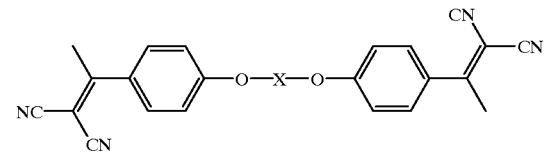

| Compound | X | $\lambda_{max}$ | $E^1_1$ |
|---|---|---|---|
| 1 | —[CH$_2$]$_2$— | 334 | 885 |
| 2 | —[CH$_2$]$_4$— | 336 | 902 |
| 3 | —[CH$_2$]$_6$— | 336 | 780 |
| 4 | —CH$_2$—CH$_2$—CH(CH$_3$)—CH$_2$—CH$_2$— | 336 | 900 |
| 5 | —CH$_2$—C(CH$_3$)$_2$—CH$_2$— | 336 | 803 |
| 6 | —[CH$_2$]$_8$— | 338 | 760 |
| 7 | —[CH$_2$]$_{10}$— | 336 | 730 |

Example 2

Standardized Method for Photostability Determination (Suntest)

A 5% by weight alcoholic solution of the sunscreen to be tested is applied, using an Eppendorf pipette (20 μl), to the milled area on a small glass plate. Owing to the presence of the alcohol, the solution is distributed uniformly on the roughened glass surface. The amount applied corresponds to the amount of sunscreen required to obtain an average sun protection factor in suncreams. In the test, 4 glass plates are irradiated each time. The evaporation time and the irradiation each last for 30 minutes. The glass plates are cooled slightly during the irradiation by a water cooling system located at the base of the Suntest apparatus. The temperature inside the Suntest apparatus during the irradiation is 40° C. After the samples have been irradiated, they are washed with ethanol into a dark 50 ml graduated flask and measured using a photometer. The blank samples are applied in the same way to glass plates and evaporated at room temperature for 30 minutes. Like the other samples, they are washed off with ethanol and diluted to 100 ml and measured.

Comparison—Photostability:

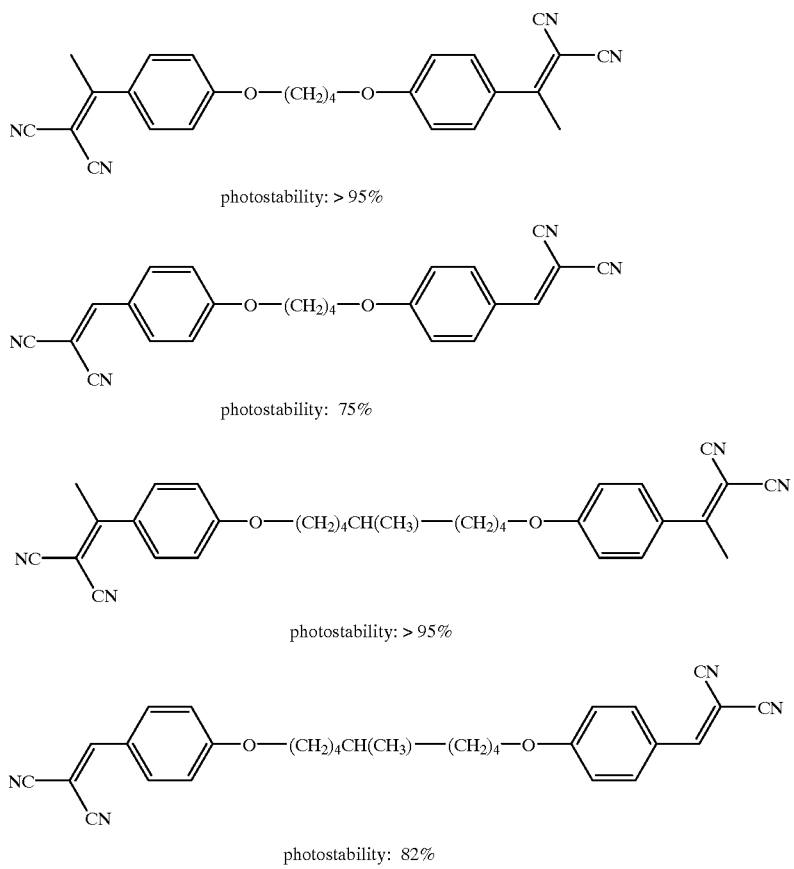

General Method for Preparing Emulsions for Cosmetic Purposes

All of the oil-soluble ingredients are heated to 85° C. in a stirred vessel. When all the ingredients have melted or are present as liquid phase, the aqueous phase is incorporated with homogenization. The emulsion is cooled to about 40° C. with stirring, is perfumed and homogenized, and is then cooled to 25° C. with continuous stirring.

PREPARATIONS

Example 3

Lip Care Composition
Mass Content
  % by weight
  ad 100 eucerinum anhydricum
  10.00 glycerol
  10.00 titanium dioxide
  5.00 compound No. 2 in Table 3
  8.00 octyl methoxycinnamate
  5.00 zinc oxide
  4.00 castor oil
  4.00 pentaerythrithityl stearate/caprate/caprylate/adipate
  3.00 glyceryl stearate SE
  2.00 beeswax
  2.00 microcrystalline wax
  2.00 quaternium-18 bentonite
  1.50 PEG-45/dodecyl glycol copolymer Example 4

Lip Care Composition
Mass Content
  % by weight
  ad 100 eucerinum anhydricum
  10.00 glycerol
  10.00 titanium dioxide
  5.00 compound No. 4 in Table 3
  8.00 octyl methoxycinnamate
  5.00 zinc oxide
  4.00 castor oil
  4.00 pentaerythrithyl stearate/caprate/caprylate/adipate
  3.00 glyceryl stearate SE
  2.00 beeswax
  2.00 microcrystalline wax
  2.00 quaternium-18 bentonite
  1.50 PEG-45/dodecyl glycol copolymer Example 5

Sunblocker Composition with Micropigments
Mass Content
  % by weight
  ad 100 water
  10.00 octyl methoxycinnamate
  6.00 PEG-7 hydrogenated castor oil 6.00 titanium dioxide
5.00 compound No. 2 in Table 3
5.00 mineral oil
5.00 isoamyl p-methoxycinnamate
5.00 propylene glycol
3.00 jojoba oil
3.00 4-methylbenzylidenecamphor
2.00 PEG-45/dodecyl glycol copolymer
1.00 dimethicone
0.50 PEG-40 hydrogenated castor oil
0.50 tocopheryl acetate
0.50 phenoxyethanol
0.20 EDTA

Example 6

Sunblocker Composition with Micropigments
Mass Content
% by weight
ad 100 water
10,00 octyl methoxycinnamate
6.00 PEG-7 hydrogenated castor oil
6.00 titanium dioxide
5.00 compound No. 4 in Table 3
5.00 mineral oil
5.00 isoamyl p-methoxycinnamate
5.00 propylene glycol
3.00 jojoba oil
3.00 4-methylbenzylidenecamphor
2.00 PEG-45/dodecyl glycol copolymer
1.00 dimethicone
0.50 PEG-40 hydrogenated castor oil
0.50 tocopheryl acetate
0.50 phenoxyethanol
0.20 EDTA

Example 7

Non-greasy Gel
Mass Content
30 % by weight
ad 100 water
8.00 octyl methoxycinnamate
7.00 titanium dioxide
5.00 compound No. 2 in Table 3
5.00 glycerol
5.00 PEG-25 PABA
1.00 4-methylbenzylidenecamphor
0.40 acrylate $C_{10}$–$C_{30}$ alkyl acrylate crosspolymer
0.30 imidazolidinylurea
0.25 hydroxyethylcellulose
0.25 sodium methylparaben
0.20 disodium EDTA
0.15 fragrance
0.15 sodium propylparaben
0.10 sodium hydroxide

Example 8

Non-greasy Gel
Mass Content
% by weight
ad 100 water
8.00 octyl methoxycinnamate
7.00 titanium dioxide
5.00 compound No. 4 in Table 3
5.00 glycerol
5.00 PEG-25 PABA
1.00 4-methylbenzylidenecamphor
0.40 acrylate $C_{10}$–$C_{30}$ alkyl acrylate crosspolymer
0.30 imidazolidinylurea
0.25 hydroxyethylcellulose
0.25 sodium methylparaben
0.20 disodium EDTA
0.15 fragrance
0.15 sodium propylparaben
0.10 sodium hydroxide

Example 9

Sun Cream (SPF 20)
Mass Content
% by weight
ad 100 water
8.00 octyl methoxycinnamate
8.00 titanium dioxide
6.00 PEG-7-hydrogenated castor oil
5.00 compound No. 2 in Table 3
6.00 mineral oil
5.00 zinc oxide
5.00 isopropyl palmitate
5.00 imidazolidinylurea
3.00 jojoba oil
2.00 PEG-45/dodecyl glycol copolymer
1.00 4-methylbenzylidenecamphor
0.60 magnesium stearate
0.50 tocopheryl acetate
0.25 methylparaben
0.20 disodium EDTA
0.15 propylparaben

Example 10

Sun Cream (SPF 20)
Mass Content
% by weight
ad 100 water
8.00 octyl methoxycinnamate
8.00 titanium dioxide
6.00 PEG-7 hydrogenated castor oil
5.00 compound No. 4 in Table 3
6.00 mineral oil
5.00 zinc oxide
5.00 isopropyl palmitate
5.00 imidazolidinylurea
3.00 jojoba oil
2.00 PEG-45/dodecyl glycol copolymer 1.00 4-methylbenzylidenecamphor
0.60 magnesium stearate
0.50 tocopheryl acetate
0.25 methylparaben
0.20 disodium EDTA
0.15 propylparaben

Example 11

Water-Resistant Suncream
Mass Content
% by weight
ad 100 water
8.00 octyl methoxycinnamate
5.00 PEG-7 hydrogenated castor oil
5.00 propylene glycol
4.00 isopropyl palmitate
4.00 caprylic/capric triglyceride
5.00 compound No. 2 in Table 3
4.00 glycerol
3.00 jojoba oil
2.00 4-methylbenzylidenecamphor
2.00 titanium dioxide
1.50 PEG-45/dodecyl glycol copolymer
1.50 dimethicone
0.70 magnesium sulfate
0.50 magnesium stearate
0.15 fragrance

Example 12

Water-Resistant Suncream
Mass Content
% by weight
ad 100 water
8.00 octyl methoxycinnamate
5.00 PEG-7 hydrogenated castor oil
5.00 propylene glycol
4.00 isopropyl palmitate
4.00 caprylic/capric triglyceride
5.00 compound No. 4 in Table 3
4.00 glycerol
3.00 jojoba oil
2.00 4-methylbenzylidenecamphor
2.00 titanium dioxide
1.50 PEG-45/dodecyl glycol copolymer
1.50 dimethicone
0.70 magnesium sulfate
0.50 magnesium stearate
0.15 fragrance

Example 13

Sunmilk (SPF 6)
Mass content
% by weight
ad 100 water
10.00 mineral oil
6.00 PEG-7 hydrogenated castor oil
5.00 isopropyl palmitate
3.50 octyl methoxycinnamate
5.00 compound No. 2 in Table 3
3.00 caprylic/capric triglyceride
3.00 jojoba oil
2.00 PEG-45/dodecyl glycol copolymer
0.70 magnesium sulfate
0.60 magnesium stearate
0.50 tocopheryl aceta 1
0.30 glycerol
0.25 methylparaben
0.15 propylparaben
0.05 tocopherol

Example 14

Sunmilk (SPF 6)
Mass Content
% by weight
ad 100 water
10.00 mineral oil
6.00 PEG-7 hydrogenated castor oil
5.00 isopropyl palmitate
3.50 octyl methoxycinnamate
5.00 compound No. 4 in Table 3
3.00 caprylic/capric triglyceride
3.00 jojoba oil
2.00 PEG-45/dodecyl glycol copolymer
0.70 magnesium sulfate
0.60 magnesium stearate
0.50 tocopheryl acetate
0.30 glycerol
0.25 methylparaben
0.15 propylparaben
0.05 tocopherol

We claim:

1. A method for protecting the skin or hair from the effects of solar rays which comprises applying to the skin or hair an effective amount of at least one of the dimeric α alkylstyrene derivatives of the formula I

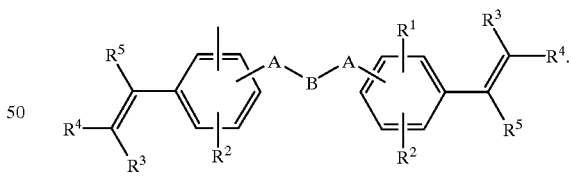

in which the substituents independently of one another have the following meanings:

$R^1$ and $R^2$ are hydrogen, OH, $NH_2$, $C_1$–$C_{12}$-alkyl, $C_1$–$C_{12}$-alkoxy, $C_1$–$C_{12}$-alkylamino, $C_1$–$C_{12}$-dialkylamino, substituents which confer solubility in water, chosen from the group consisting of carboxylate, sulfonate or ammonium radicals;

$R^3$ is $COOR^6$, $COR^6$, $CONR^6R^7$, CN;

$R^4$ is $COOR^6$, $COR^6$, $CONR^6R^7$, CN;

$R^5$ is $C_1$–$C_{12}$-alkyl, $R^6$ and $R^7$ are hydrogen, $C_1$–$C_{12}$-alkyl, $C_2$–$C_{10}$-alkenyl, $C_3$–$C_{10}$-cycloalkyl, $C_3$–$C_{10}$-cycloalkenyl, aryl, heteroaryl, optionally substituted;

A is O, S, N—R$^8$;

B is C$_1$–C$_{12}$-alkylene, C$_4$–C$_{12}$-cycloalkylene, C$_8$–C$_{22}$-aralkylene, C$_9$–C$_{21}$-monooxoaralkylene, [—X—]$_n$—Y;

R$^8$ is hydrogen, C$_1$–C$_{12}$-alkyl;

X is —CH$_2$—CH$_2$—Z—, —CH$_2$—CH$_2$—CH$_2$—Z—, —CH(CH$_3$)—CH$_2$—Z—, —CH$_2$—CH$_2$—CH$_2$—CH$_2$—Z—, CH$_2$—CH(CH$_2$—CH$_3$)—Z—;

Y is —CH$_2$—CH$_2$—, —CH$_2$—CH$_2$—CH$_2$—, —CH(CH$_3$)—CH$_2$—, —CH$_2$—CH$_2$—CH$_2$—CH$_2$—, —CH$_2$—CH(CH$_2$—CH$_3$)—;

z is O, S;

n is 1 to 150, where, in each case, two of the radicals R$^1$, R$^2$ and R$^8$ together with the aromatic ring to which they are bonded can form a 5- or 6-membered ring.

2. A method as claimed in claim 1, where the substituents have the following meanings:

R$^1$ and R$^2$ are hydrogen, C$_1$–C$_8$-alkyl, C$_1$–C$_8$-alkoxy, substituents which confer solubility in water, chosen from the group of carboxylate, sulfonate or ammonium radicals;

R$^3$ is COOR$^6$, CN;

R$^4$ is COOR$^6$, CN;

R$^5$ is C$_1$–C$_6$-Alkyl;

R$^6$ is C$_1$–C$_{12}$-Alkyl;

A is O;

B is C$_1$–C$_{12}$-alkylene, C$_8$–C$_{22}$-aralkylene, C$_4$–C$_{12}$-cycloalkylene, [—X—]$_n$—Y;

X is —CH$_2$—CH$_2$—O—, —CH$_2$—CH$_2$—CH$_2$—O—, —CH(CH$_3$)—CH$_2$—O—, —CH$_2$—CH$_2$—CH$_2$—CH$_2$—O—, —CH$_2$—CH(CH$_2$—CH$_3$)—O—;

Y is —CH$_2$—CH$_2$—, —CH$_2$—CH$_2$—CH$_2$—, —CH(CH$_3$)—CH$_2$—, —CH$_2$—CH$_2$—CH$_2$—CH$_2$—, —CH$_2$—CH(CH$_2$—CH$_3$)—;

n is 1 to 20.

3. A method as claimed in claim 1, where the substituents have the following meanings:

R$^1$ and R$^2$ are hydrogen, C$_4$–C$_8$-alkyl, C$_4$–C$_8$-alkoxy, substituents which confer solubility in water, chosen from the group consisting of carboxylate, sulfonate or ammonium radicals;

R$^3$ and R$^4$ are CN;

R$^5$ is C$_1$–C$_6$-alkyl;

A is O;

B is C$_1$–C$_{12}$-alkylene, [—X—]$_n$—Y;

X is —CH$_2$—CH$_2$—O—, —CH(CH$_3$)—CH$_2$—O—;

Y is —CH$_2$—CH$_2$—, —CH(CH$_3$)—CH$_2$—;

n is 1 to 20.

4. A method as claimed in claim 1, wherein the dimeric α alkylstyrene derivatives of the formula I have the following structural formula

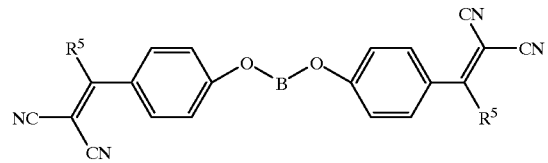

where the substituents have the following meanings:

R$^5$ is C$_1$–C$_6$-alkyl;

B is C$_1$–C$_{12}$-alkylene.

5. A cosmetic or pharmaceutical preparation comprising suncreens for protecting the human epidermis or human hair from UV light in the range from 280 to 400 nm, which comprises, in a cosmetically or pharmaceutically suitable carrier, alone or together with compounds which absorb in the UV region and are known for cosmetic and pharmaceutical preparations, an effective amount of compounds of the formula I

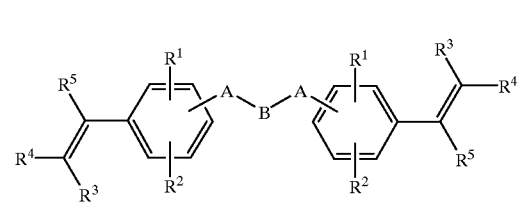

in which the substituents are as defined in claim 1, as photostable UV filters.

6. A cosmetic or pharmaceutical preparation comprising sunscreens as claimed in claim 5, comprising, as UV-A filter, compounds of the formula Ia.

* * * * *